(12) United States Patent
Griffin et al.

(10) Patent No.: US 8,207,492 B2
(45) Date of Patent: Jun. 26, 2012

(54) CHEMICAL DETECTION SYSTEM AND METHOD USING A CAPACITIVE TRANS IMPEDANCE AMPLIFIER

(75) Inventors: Matthew Todd Griffin, Indian Land, SC (US); John Michael Alfred Petinarides, Waxhaw, NC (US); Paul Joseph Rauch, Charlotte, NC (US); Jerome Paul Dahl, Stanfield, NC (US); Robert Francis McAtee, Lake Wylie, SC (US)

(73) Assignee: Chemring Detection Systems, Inc., Charlotte, NC (US)

( * ) Notice: Subject to any disclaimer, the term of this patent is extended or adjusted under 35 U.S.C. 154(b) by 522 days.

(21) Appl. No.: 12/355,560

(22) Filed: Jan. 16, 2009

(65) Prior Publication Data

US 2009/0212207 A1    Aug. 27, 2009

Related U.S. Application Data

(63) Continuation-in-part of application No. 11/748,258, filed on May 14, 2007.

(60) Provisional application No. 61/021,575, filed on Jan. 16, 2008.

(51) Int. Cl.
*B01D 59/44* (2006.01)
*H01J 49/00* (2006.01)

(52) U.S. Cl. ........ 250/282; 250/281; 250/283; 250/287; 250/288; 250/289; 250/290; 250/291; 250/292; 250/397; 330/86; 330/282; 330/308

(58) Field of Classification Search .......... 250/281–283, 250/287–292, 397; 330/86, 282, 308
See application file for complete search history.

(56) References Cited

U.S. PATENT DOCUMENTS

| | | | |
|---|---|---|---|
| 6,809,313 B1 * | 10/2004 | Gresham et al. | 250/287 |
| 2005/0156107 A1 * | 7/2005 | Miller et al. | 250/293 |
| 2007/0228269 A1 | 10/2007 | Miller et al. | |

OTHER PUBLICATIONS

Notification of Transmittal of the International Search Report and the Written Opinion of the International Searching Authority, or the Declaration, dated Feb. 25, 2009.
Notification of Transmittal of the International Search Report and the Written Opinion of the International Searching Authority, or the Declaration, dated Mar. 6, 2009.
Notification of Transmittal of the International Search Report and the Written Opinion of the International Searching Authority, or the Declaration, dated Feb. 20, 2009.

* cited by examiner

*Primary Examiner* — Jack Berman
*Assistant Examiner* — Meenakshi Sahu
(74) *Attorney, Agent, or Firm* — Hunton & Williams LLP

(57) ABSTRACT

The exemplary embodiments provide a method, system, and device for identifying chemical species in a sample. According to one embodiment, the method, system, and device may include introducing a sample gas into a differential ion mobility device, ionizing at least a portion of the sample gas to generate at least one ion species, filtering the at least one ion species between a pair of filter electrodes, generating a detection signal in response to the at least one ion species depositing a charge on a collector electrode, and detecting a spectral peak associated with the at least one ion species.

21 Claims, 11 Drawing Sheets

DRY
0.14 mg/m³ GB, Unit 3,
Pos-Vn =700 RIP = -5.25V

WET
0.14 mg/m³ GB, Unit 2,
Pos-Vn =700 RIP = -9.50V

CHEMICAL DETECTION SYSTEM AND METHOD USING A CAPACITIVE TRANS IMPEDANCE AMPLIFIER

RELATED APPLICATIONS

This application also claims the benefit of U.S. Provisional Application No. 61/021,575, filed Jan. 16, 2008, which is incorporated by reference herein in its entirety. This application is a continuation-in-part of U.S. application Ser. No. 11/748,258, filed on May 14, 2007, entitled "Method and System for Detecting Vapors," which is incorporated by reference herein in its entirety.

FIELD OF THE INVENTION

The exemplary embodiments relate generally to a system, method and device to identify compounds in a sample gas based on ion mobility characteristics. More particularly, the present embodiments relate to a device to identify compounds using differential ion mobility spectrometry.

BACKGROUND OF THE INVENTION

Current events underscore the need for an improved and inexpensive analytical device capable of rapidly, reliably, and accurately detecting explosives, toxic chemicals and biologics, chemical warfare agents, and other harmful materials. Spectrometers based on ion mobility have been previously developed to serve this purpose, but technological improvements are still needed to reduce detection time, increase sensitivity, enable environment adaptability, reduce noise interference, improve prediction accuracy, and reduce power consumption.

Conventional spectrometers typically employ either ion-mobility spectrometry (IMS) or differential ion mobility spectrometry (DMS) as the broad method by which they identify compounds in a sample gas taken from an ambient environment. Conventional IMS devices, which are well known in the art, are based on time-of-flight (TOF-IMS) analysis. TOF-IMS identifies compounds by measuring the time it takes ions to travel through a drift tube, usually on the order of milliseconds, from a shutter-gate to a detector electrode. The drift time is dependent on the mobility of ions in a linear, low electric field, which accelerates the ions in the drift tube. The measured drift time is characteristic of the ion species present in the sample. In IMS systems, an ion's mobility coefficient is independent of the electric field strength but its velocity is proportional to the electric field strength.

Though typical IMS and DMS based devices share many of the same system components (inlet system, ionization source, readout electronics) DMS devices operate very differently. DMS devices characterize chemical substances using differences in the gas phase mobilities of ions in alternating, high-frequency, asymmetric electric fields. Ions are separated as they are carried by drift gas between two-parallel plates or filter electrodes. At higher electric field strengths there is a nonlinear dependence of ion mobility. A high-frequency asymmetric electric field is produced by applying a high-frequency asymmetric differential potential between the plates. An equivalent field could be produced by applying a differential potential to both plates relative to ground, or to one of the plates with the other grounded. This applied field, referred to as the separation or dispersion voltage, causes ions to oscillate perpendicular to the gas flow. Some ions traverse the filter electrodes, while others gradually move towards one of the electrodes and eventually collide with an electrode, which neutralize the electric charge in such ions. Only ions with a net velocity or differential mobility of zero transverse to the applied electric field will pass through the electrodes.

The net migration of the ions can be corrected with a compensation voltage (Cv), which is a weak dc voltage superimposed on the high-frequency, asymmetric electric field, to correct the path ions travel so they do not move towards an electrode.

Various techniques of DMS have been developed, including field ion spectrometry (FIS), transverse field compensation ion mobility spectrometry, ion non-linearity drift spectrometer, field asymmetric ion mobility spectrometry (FAIMS), and radio frequency ion mobility spectrometry (RFIMS), among others.

However, current devices that use DMS to identify compounds, although improved over conventional TOF-IMS systems, still have deficiencies that must be improved, like reductions in detection time, noise, and power consumption; increases in sensitivity; and improvements in environment adaptability, and prediction accuracy.

SUMMARY OF THE INVENTION

In a first exemplary embodiment, a method is provided for identifying chemical species in a sample. The method includes introducing a sample gas into a differential ion mobility device, ionizing at least a portion of the sample gas to generate at least one ion species, filtering the at least one ion species between a pair of filter electrodes, generating a detection signal using a capacitance trans impedance amplifier (CTIA) in response to the at least one ion species depositing a charge on a collector electrode, the CTIA sending the detection signal to a signal processor, and detecting a spectral peak associated with the at least one ion species by processing the detection signal and referencing a data store to identify an unknown compound in the species.

In another exemplary embodiment, a device is provided for identifying chemical species in a sample gas. The device includes an inlet adapted to receive a sample gas, the inlet being selectively separated from an ionization region that ionizes the sample gas to generate ions, a filter having at least a pair of oppositely disposed filter electrodes defining an analytical gap between which a substantially asymmetric field is generated, the substantially asymmetric field being controllable by a signal generator, wherein the filter separates the ions based on ion mobility characteristics, at least one collector electrode adapted to receive the ions, the collector being coupled to an capacitive trans impedance amplifier (CTIA), and a signal processor adapted to receive an output voltage generated by the CTIA in order to detect a spectral peak associated with the ions.

BRIEF DESCRIPTION OF THE FIGURES

Advantages of the exemplary embodiments will be apparent to those of ordinary skill in the art from the following detailed description together with the appended drawings, in which like reference numerals are used to indicate like elements.

DESCRIPTION OF THE PREFERRED EMBODIMENTS

The following description provides a description and understanding of exemplary embodiments for a system, method, and device to identify compounds, in a sample gas, based on ion mobility characteristics. The system and method, however, are not limited to these exemplary embodiments. Moreover, one of ordinary skill in the art, after reading the following description, will appreciate the use of the exemplary embodiments for their intended purpose and benefit in a number of alternative embodiments.

The exemplary embodiments described herein have particular application to high-frequency ion-mobility spectrometry. The exemplary embodiments provide for an improved system and method to identify and discriminate between compounds that exist in a sample gas analyzed using differential mobility spectrometry. Generally, the exemplary embodiments describe a system and method that collects a sample gas, ionizes that sample gas into ions (also referred to as analytes), carries those ions typically with a carrier gas through a filtering section that applies an alternating, asymmetric electric field to the ions, and detects or identifies compounds based on ion mobility characteristics. The applied electric field has a varying influence on the unknown ions traveling between the filter electrodes, and the behavior of the ions, in response to the applied electric field, allows for different species of ions to be identified by comparing detected ion peak locations to known data stored within a processor in the device.

Figure 1:
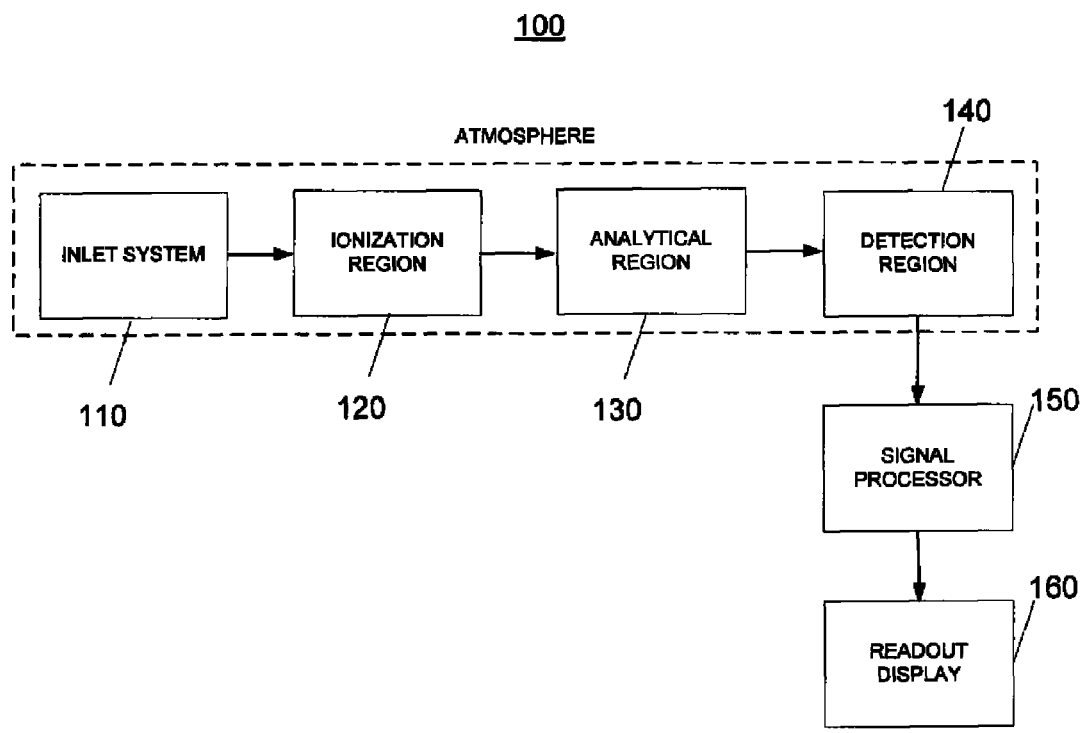
FIG. 1 illustrates a block diagram of an exemplary device for detecting chemical species based on analytes in a carrier gas.

FIG. 1 illustrates a block diagram that shows an exemplary embodiment of a device 100 that may be used to analyze a sample gas, and directly or indirectly identify one or more compounds contained therein. A sample gas may be introduced into the device 100 from an ambient air environment. In an exemplary embodiment, the device 100 may be a differential mobility spectrometer (DMS) detector, a field asymmetric ion mobility spectrometry (FAIMS) detector, a field ion spectrometry (FIS) detector, a radio frequency ion mobility spectrometry (RFIMS), or any other type of detector capable of analyzing a gas and identifying compounds based on ion mobility characteristics.

In operation, sample gas may be introduced into the inlet region 110 of the device 100 from an ambient air environment. The sample gas flows into an ionization region 120. There, one or more compounds in the sample may be ionized by an ionization source to generate ions or analytes of chemical species present in the sample gas. The ions may be carried by a carrier gas from the ionization region 120 to the analytical region 130, which typically consists of two, oppositely disposed filter electrodes (not shown) that define an analytical gap. In the analytical gap, an alternating, asymmetric field may be applied between the filter electrodes to filter the ions based on differences in ion mobility, which may be influenced by ion size, shape, mass, and charge. Ions that pass through the analytical region 130 then flow to the detection region 140, which may consist of a pair of oppositely charged collector electrodes (not shown), one positive and one negative. A detection signal may be generated using a capacitive trans impedance amplifier (CTIA), as ions deposit their charges on the collector electrodes. Stated differently, the CTIA amplifies the signal from the collector electrodes and provides an amplified signal representing the detected ion current to a signal processor 150. The signal may then be processed using the signal processor 150 to identify compounds in the sample gas. The signal processor may communicate those identifications to a readout display 160 where they may be displayed. In an exemplary embodiment, the readout display 160 may be an LCD or other display technology that displays a visual alert with information regarding the identifications. In another exemplary embodiment, the readout display 160 may be a speaker that emits an audible sound for identifying purposes. Though the device 100 may be described as having regions, such regions are for description purposes only, are not limited to actual physical locations within the device 100, and may overlap or be combined. Each region within the device 100 will be further described in detail below.

The device 100 may be adapted to detect various species within gas sampled from an ambient air environment. The species that device 100 may be capable of identifying may include, but are not limited to, chemical warfare agents, nerve agents, blister agents, choking agents, toxic industrial chemicals (TICs), toxic industrial materials (TIMs), low vapor compounds, explosives, narcotics, biologics, pathogens, organic chemicals, inorganic chemicals, hydrocarbons, or combinations thereof.

As recited above, the device 100 may comprise a series of regions that are fluidly connected in order for the device 100 to identify one or more compounds in a sample gas. Those regions may include the inlet region 110, the ionization region 120, the analytical region 130, the detection region 140, the signal processor 150, and the readout display 160. Each subsystem may have features contained within that will be further described below.

The inlet region 110 may be the sample collection subassembly responsible for drawing a sample from the environment into the device 100. In an exemplary embodiment, the inlet region 110 may serve two functions: sample collection and introduction. The inlet region 110 may also concentrate the sample, filter the sample, or provide a selective barrier between the analytical region 130 and the environment.

Figure 2:
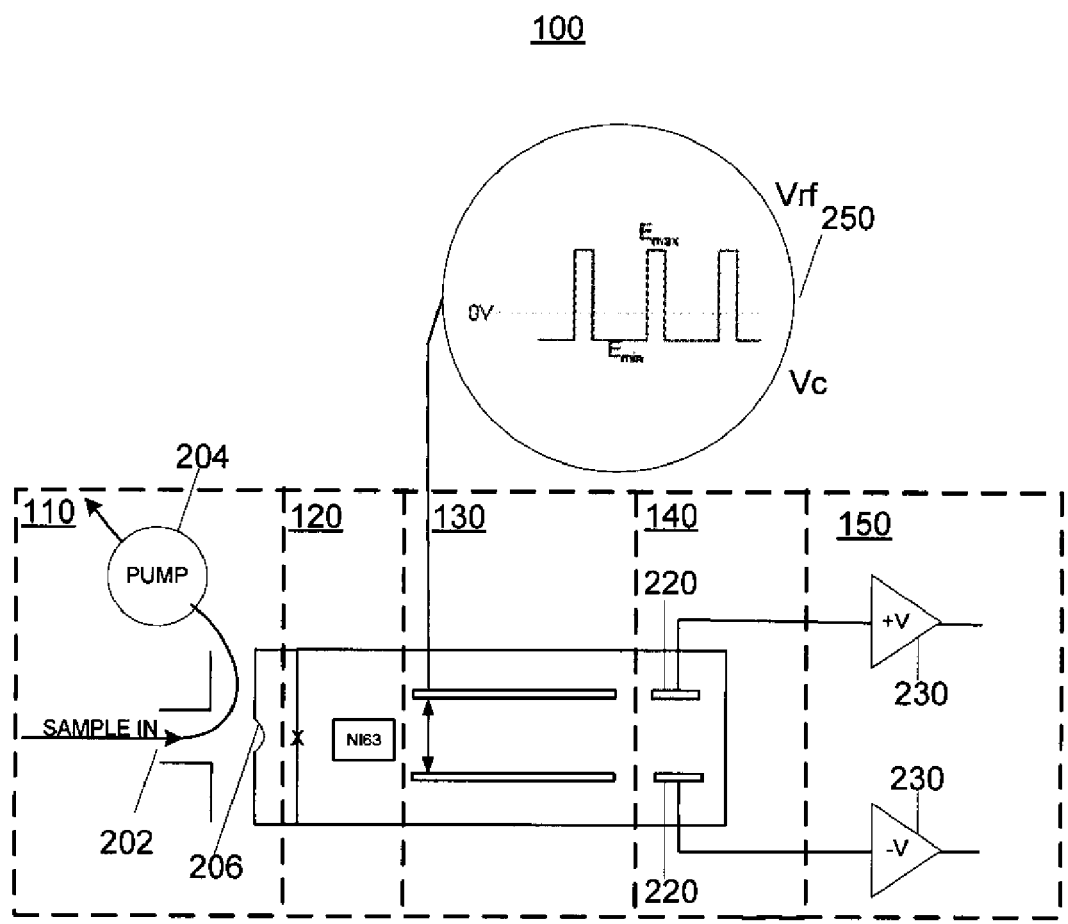
FIG. 2 illustrates a more detailed block diagram of an alternative exemplary device for detecting chemical species based on analytes in a carrier gas.

FIG. 2 illustrates a block diagram of an exemplary device for detecting chemical species based on analytes in a carrier gas. The inlet region 110 may have a inlet opening 202 adapted to receive a sample gas as input to the device 100 from the ambient environment. The inlet region 110 may comprise a heated element or other heating device, such as a heated vacuum transfer line (not shown) followed by a membrane 206. A sampling pump 204 may be coupled to an outlet (not shown), through which excess sample gas may be discharged. The pump 204 may create a vacuum for drawing the sample gas from an ambient air environment into the inlet 202. A heating element or other heating device may facilitate the flow of the sample gas through the inlet region 110, and may prevent chemical species within the sample gas from adhering to a wall in the device 100, for example. The vacuum side of the pump 204 may be attached to the heated transfer line to pull a sample from the environment through the heated transfer line and across the membrane 206. Not all of the sample, however, may permeate through the membrane 206, and any excess sample gas will be exhausted back into the environment, bypassing other subsystems in the device 100.

The membrane 206 may be gas-permeable and may reside inside of the inlet region 110, separating the inlet region 110 from the ionization region 120. The membrane 206 may permit some or all of the molecules or compounds in the sample gas to diffuse across the membrane 206 and flow into the ionization region 120. The membrane 206 may selectively block certain molecules from passing though to the ionization region 120. The membrane 206 may be one of two types of membrane: a thin film membrane or an oil membrane. A thin film membrane may comprise a solid material stretched to a known thickness with a known permeability. An oil membrane may be a thin, porous substrate coated or conditioned, or both, with oil. Integrating a membrane of either type into the inlet region 110 may permit for a more efficient transfer of the sample gas through the device 100. The membrane 206 may be designed such that it eliminates reduced permeation rates for chemical species of interest, which, if not eliminated, may cause a decrease in sensitivity. The membrane 206 may be designed to reduce the chance that species chemically bind to the membrane 206, which may degrade the membrane 206. The membrane 206 may be configured to withstand a range of temperatures and environments that the device 100 may be exposed to and used in. The membrane 206 may further prevent contaminants from being introduced into the ionization region 120.

The membrane 206 may prevent moisture from passing through the inlet region 110 to the ionization region 120. As will be discussed below, it has been discovered that moisture significantly impacts the spectra of identified ions, and therefore, it may be desirable to maintain the moisture level within a known range. The membrane 206 may be configured such that it helps maintain a moisture level within the device 100 of between about 100 parts per million (ppm) and about 1000 ppm, for example. However, the range of moisture level in the device 100 may be changed as necessary or desired. The membrane 206 may be made of any suitable material, thickness, or surface area, to improve its permeation characteristics to allow molecules of interest to pass efficiently from the inlet region 110 to the ionization region 120. The temperature may be controlled across the membrane 206, and it may be held at various temperatures, either uniform or gradient. The type, geometry, and location of the membrane 206 used in the inlet system 110 may contribute to a quicker and more reliable detection process and result. A specific membrane or sample control mechanism may be selected for particular detection applications. The membrane temperature may be optimized/set based on the characteristics of the analyte of interest. As analytes may be optimized at different temperatures to one another, it is sometimes possible to optimize the membrane conditions for a range of analytes by creating a temperature gradient across the membrane by holding the outer supported part of the membrane at one temperature and allowing the center region to stabilize at another temperature.

Still referring to FIG. 2, the inlet region 110 may be optimized in a variety of ways in order for the device 100 to operate efficiently, consistently, and reliably. For example, problems that may be avoided by an optimizing the inlet region 110 include substantially reducing pockets of the sample gas in the interior of the inlet region 110. These pockets may cause an initial decrease in the sample gas available for permeation across the membrane 206, which may later lead to false signals due to extended clear down times as the pocket of sample gas slowly diffuses from the inlet walls through the membrane 206 to the ionization region 120 over time. Other ways to optimize the inlet region 110, may include selecting a durable and reliable membrane material for the given or expected sample environment, establishing a temperature gradient through the inlet region 110, and maintaining a substantially constant rate at which the sample may be pumped through the inlet region 110.

Figure 3:
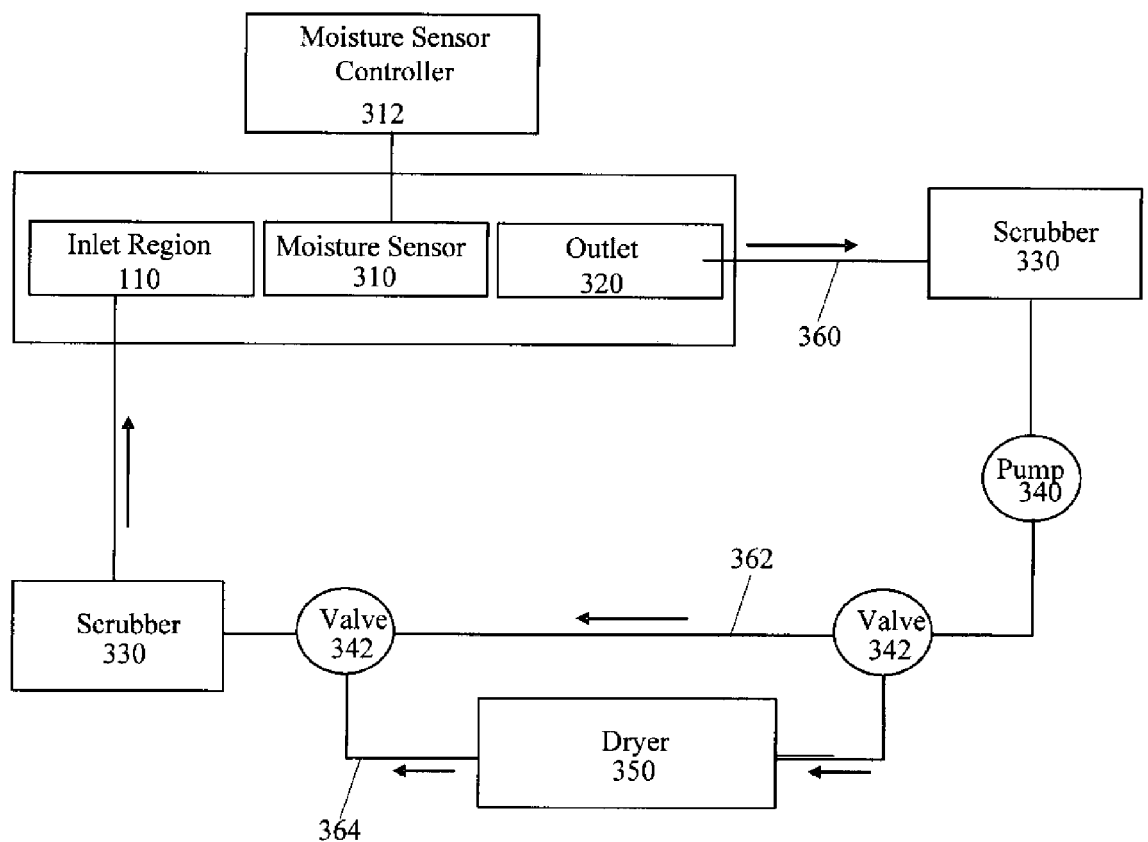
FIG. 3 illustrates a block diagram of an exemplary moisture control system for use in an exemplary device for detecting chemical species based on analytes in a carrier gas.

FIG. 3 is a block diagram of an exemplary embodiment of a moisture control system 300 used in the device 100. The device 100 may be adapted to control the moisture or moisture content of the gas passing through the device 100. For example, the device 100 may require that the moisture content of the carrier gas, which carries the ions and flows through the analytical region 120, to be within a particular range, e.g., 100 ppm to 1000 ppm.

In an exemplary embodiment, the moisture control system 300 may include a moisture sensor 310 connected to a moisture sensor controller 312. The moisture sensor 310 may be suitably disposed in the gas flow. For example, the moisture sensor 310 may be disposed in the analytical region 130 of the device 100. The moisture sensor 310 senses at least one parameter of the gas and outputs a signal representing the at least one parameter to a moisture sensor controller 312. The moisture sensor controller 312 analyzes the at least one parameter the moisture content of the gas. Any known sensor may be used to collect data suitable for ascertaining the moisture content in the gas. The moisture content or moisture level may be adjusted based on the moisture sensed by the moisture sensor 312.

In another embodiment, the moisture sensor 310 may not be a physical component or sensor that is incorporated into the device. Instead, monitoring the water/vapor content of the gas may be accomplished by the device 100 itself. For example, a reactant ion peak (RIP), which is explained in further detail below, is sensitive to changes in the moisture content of the gas—i.e., the positive and negative RIP of a DMS instrument using water chemistry is very sensitive to changes in moisture content. Therefore, the properties of the device—the positive ion peak location ($V_c$)—may be used as the moisture control for the gas. In other words, the moisture can be controlled by monitoring the position of the RIP position.

The moisture control system 300 may include a gas flow line 360. Gas may pass through an outlet 320 into the gas flow line 360. As shown in FIG. 3, the gas may circulate through the gas flow line 360 in a closed loop manner. In other words, the gas may pass out of the outlet 320 into the gas flow line 360, then pass through various components disposed along the gas flow line 360, and back into the inlet region 110 in the device 100. In one embodiment, the gas flows into the inlet region 100 across the back side of the membrane 206 (referring to FIG. 2). During such circulation, the moisture in the gas may be controlled. A pump 340 may be used to pump the gas through the gas flow line 360.

The moisture control system 300 may include at least one scrubber 330. In an exemplary embodiment, the moisture control system 300 may have two scrubbers 330 disposed along the gas flow line 360, as shown in FIG. 3. The one or more scrubbers 330 may be provided to remove contaminates from the circulating gas. The scrubber 130 may be disposed in the gas flow line 360 as desired. For example, a scrubber 330 may be disposed immediately after the gas exits the outlet 320 or a scrubber 330 may be disposed immediately before the gas enters the inlet region 110.

As disclosed herein, a "scrubber" may be described as any medium or substance capable of removing contaminates from the gas. The scrubber may be used to remove such contaminates, and not to remove moisture from the gas. Accordingly, the scrubber 330 may comprise any medium, such as activated charcoal, capable of removing analytes and other contaminating materials from the gas. In an exemplary embodiment, the scrubber 330 may be provided to remove analytes or contaminating vapors from the carrier gas (used to transport ions through an analytical region of a differential mobility spectrometer) in a spectrometer. It is expected that any such scrubber material will have some capacity to absorb moisture. However, in the applications of the moisture control system 300, it may be advantageous to use a scrubber material with a relatively low saturation point for moisture absorption. This characteristic may be useful in being able to condition the scrubber 330 to a specific level of moisture, capable of maintaining the carrier gas or other gas to within a range of moisture content, required for the optimal performance of the device 100.

The moisture control system 300 may also includes a dryer 350. As disclosed herein, a "dryer" may be described as any medium or substance capable of removing moisture from the gas. The dryer 350 may be used to remove moisture, and not to remove contaminates from the gas. In an exemplary embodiment, the dryer may include a drying agent. The dryer agent may be any material or desiccant capable of removing moisture from the gas, e.g. air or carrier gas used in the device 100. A molecular sieve, as is well known in the art, may be a very efficient dryer and may be capable of binding water molecules to itself and not releasing it back to the carrier gas until it reaches a high saturation point. A molecular sieve may be well suited to function in the moisture control system 100 to take out excess moisture from the carrier gas, and thus maintain a desired moisture level for the gas. It is recognized that a molecular sieve, or other dryer that is utilized, may also remove some contaminants.

As shown in FIG. 3, the gas flow line may include a primary pass-through line 362 and a secondary pass-through line 364. The secondary pass-through line 364 may include the dryer 350, whereas the primary pass-through line 362 may not. The carrier gas circulating through may be controlled to flow through either the primary pass-through line 362 or the secondary pass-through line 364.

A pair of dryer valves 342 may be provided to control which pass-through line the gas passes. In an exemplary embodiment, the moisture control system 300 may have a pair of valves 342. The first valve 342 may selectively control the gas flow to pass into the primary pass-through line 362 or the secondary pass-through line 364. The second valve 364 may selectively control the gas flow to exit from the primary pass-through line 362 or the secondary pass-through line 364. In an exemplary embodiment, the dryer valves 342 may be controlled by the moisture sensor controller 312. As described above, the moisture sensor 310, disposed in the gas flow, senses at least one parameter of the gas and outputs this information to the moisture sensor controller 312. The at least one parameter may provide the data to the moisture sensor controller 312 by which the moisture sensor controller 312 may determine the moisture content of the gas. Based on the determination of the moisture in the gas, the moisture sensor controller 312 switches the valves 342 so that the gas flows through either the primary pass-through line 362 or the secondary pass-through line 364. The moisture sensor controller 312 may maintain the moisture between an upper and a lower threshold value as desired. It is appreciated that the particular moisture range will depend on the needs of the particular conditions.

Referring back to FIGS. 1 and 2, in an exemplary embodiment, sample gas may enter may flow across the membrane 206, where sample molecules permeate from one side of the membrane 206 to the other side. A carrier gas, which may be separated from the sample gas, may then sweep across the back side of the membrane 206 and carry the sample molecules into the ionization region 120. The molecules of the sample gas passing through the membrane 206 to the ionization region 120 may be referred to as analytes. In the ionization region 120, the sample gas, carrying one or more analytes to be detected, may be subjected to an ionization source. In an exemplary embodiment, the device 100 may have more than one ionization source. The one or more ionization sources may ionize the analytes, which react in an ion reaction region, such as through atmospheric pressure chemical ionization. The one or more ionization source may be a Nickel 63 (Ni63) source, a corona, a plasma source, a UV lamp, or other known sources for ionizing chemicals. Also, the one or more ionization source may be plasma generators for ionizing the analytes. Other radioactive materials, such as, for example, Americium also may be used for as an ionization source for ionizing the analytes. The type of ionizing source may be selected based on the preferred ion affinity of the analytes, and power and life required from the ionizing source. After the analytes are ionized, they may pass through the ion reaction region and into the analyzer section 130.

Figure 4:
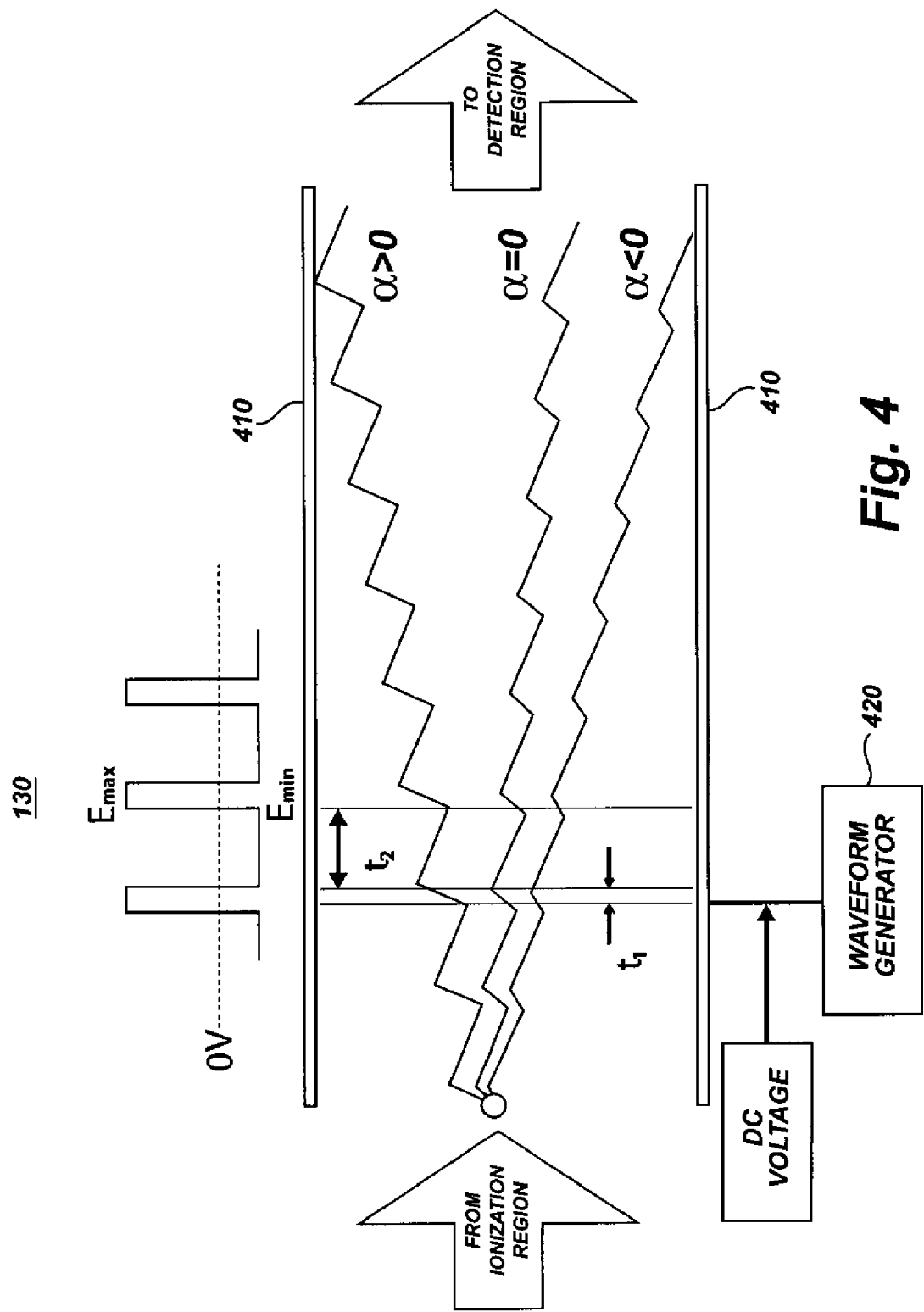
FIG. 4 illustrates an exemplary embodiment of the analytical region within the device.

FIG. 4 illustrates an exemplary analytical region 130 of an exemplary device for detecting chemical species based on analytes in a carrier gas. Referring to FIGS. 2 and 4, the analytical region 130 may be downstream of the ionization region 120 and upstream of the detection region 140. A purpose of the analytical region 130 may be to selectively separate the ion species before they collide with one or more collector electrodes 220 (shown in FIG. 2) in the detection region 140. To separate the ion species before they collide with the one or more collector electrodes (not shown), a field strength (E), generated by an asymmetric waveform generator 420, and a small DC voltage (Ec), are applied to one of two parallel filter electrodes 410. Ions pass between the filter electrodes 410, also referred to as parallel electrode plates. An alternating, asymmetric electric field, the exemplary shape of which is shown at the top of FIG. 4, may be developed between the filter electrodes 410 and be transverse to the gas flow. FIG. 2 also shows an exemplary embodiment of the asymmetric field 250 developed between the filter electrodes. The ions oscillate and move in a zigzag motion between the filter electrodes 410, as the field switches from positive to negative, toward the detection region 140. The net "drift" of an ion towards one electrode 410 or another at a field strength may be dependent on a characteristic difference between the ion's mobility at high and low fields. Ions that do not have a balance between high field and low field mobility will drift into one of the filter electrodes 410 and be neutralized.

The asymmetric waveform effectively separates ions based on their field mobility dependence. If only the variable field strength is used, the analytical gap can only "detect" ions already in equilibrium (no net drift) because all other ions will collide with the filter electrodes 410, thereby losing their charge. In other words, as charged ions pass through the analytical region 130, some are neutralized as they collide with the filter electrodes 410, while others pass to the detection region without losing their charge 140. For some ions to pass through the analytical region 130, an additional DC voltage may be applied across the filter electrodes 410 to create an additional electric field. This DC voltage may be called the compensation voltage (Ec). The compensation voltage shifts the paths of the rest of the ions through the analytical region 130 so that "unbalanced" ions may selectively become balanced and will pass through to the detection region 140.

In the analytical region 130, the concentration of ions of one species reaching the collector electrode 220 can be calculated as the following boundary value problem that is solved from t=0 to t=l/v, integrating n at the collector electrode 220 (distance l from the ionization source) over a width of −de/2 to de/2 (the effective gap):

$$\frac{\partial n}{\partial t} = \vec{\nabla}\left(n\vec{V} - D\vec{\nabla}n\right) \quad [1]$$

$$\vec{V} = K(E)\vec{E} \quad [2]$$

$$E = E(t) + E_c \quad [3]$$

$$d_e = d - \delta \quad [4]$$

$$\delta = \frac{1}{2}\int_0^{t_1+t_2} |\vec{V}|\,dt \quad [5]$$

where:
de=the "effective gap" between the parallel plates
d=the width of the gap between the parallel plates
δ=the magnitude of the oscillations between the plates in one period of the asymmetric waveform.
l=the length of the parallel plates
v=the velocity of the carrier gas through the analytical region
n=is the concentrations of ions (1 species)
t=time
$t_1$=the time under high frequency conditions (see FIG. 4)
$t_2$=the time under low frequency conditions (see FIG. 4)
V=the velocity of the ions
D=diffusion coefficient
K(E)=the field mobility dependence under the electric field E
E=the electric field between the parallel plates
E(t)=electric field of asymmetric waveform at time t
$E_c$=compensation voltage
(Note that Equation 3 must be modified for cylindrical plate geometry because the electric field is nonuniform. Also note that Equation 5 is only valid for an asymmetric waveform that is a step function. A different waveform will require a change to Equation 5.)

Figure 5:
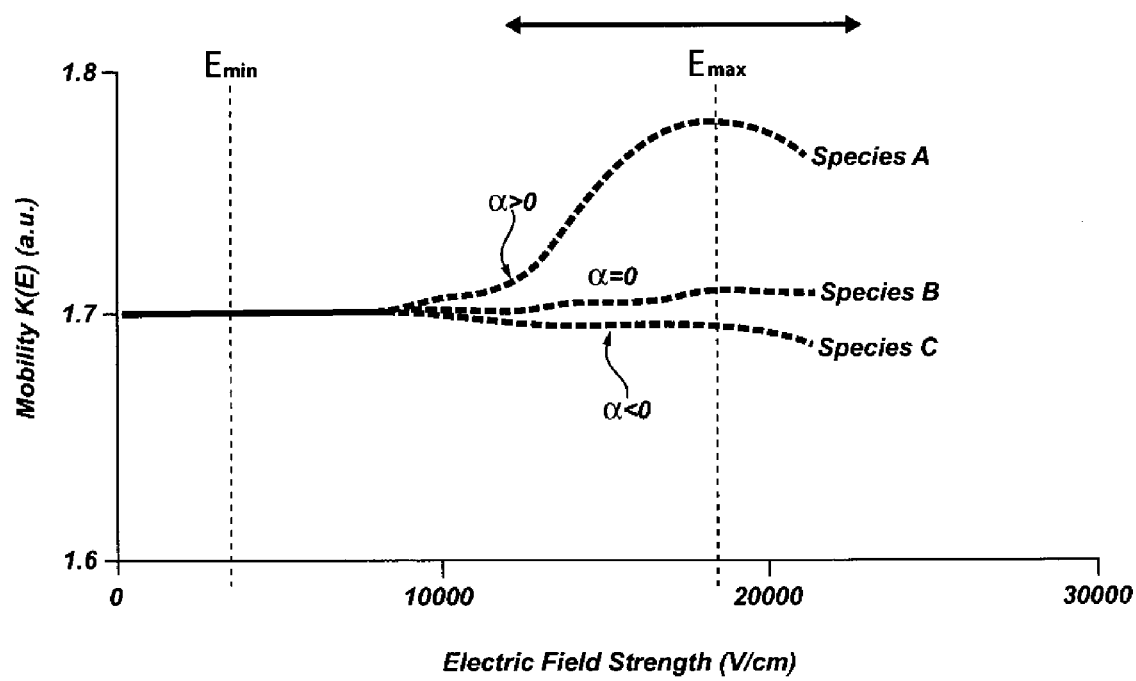
FIG. 5 illustrates a chart showing the field-dependent mobility of three different ion species under various electric fields using an exemplary vapor detector.

The field strength E(t) is a function of time because it alternates between high and low frequency fields. The mobility of ions changes with the strength of the field, and the net difference between low and high field mobility is the characteristic that is used to separate different ion species. For example, FIG. 5 depicts the mobility of three different ion species at different field strengths. Notice that mobility generally increases as the field strength increases. For some ions, however, such as Species A, as shown in FIG. 5, mobility may begin to decrease past a certain field strength. The maximum field strength that can be achieved before arcing occurs is dependent on the width between the filter electrodes 410, and the pressure within the analytical region 130. Larger gaps and higher pressures allow stronger field strengths to be used.

The compensation voltage ($E_c$ in Equation 3) is the small amount of DC voltage applied across one filter electrode 410 to bring different ion species into "equilibrium" such that those species reach the detection region 140.

The width of the analytical region 130, i.e., the distance between the filter electrodes 410, (d in Equation 4) has an effect on both the peak widths and sensitivity that are produced by the detection region 140. A smaller gap between the two filter electrodes 410 may cause more ions to be annihilated as they hit the electrodes 410. This can decrease sensitivity because some of the ions in "equilibrium" may touch the sides due to diffusion or oscillation between positive and negative fields. It can also create narrower peaks in the DMS spectra. If the gap becomes smaller than the width of the oscillations (δ in Equation 4) of an ion between positive and negative fields, then the ion will not be detected. This is because the ion may collide with a filter electrode 410 before reaching the detection region 140 (even when in equilibrium). A very large gap may increase sensitivity, but may create wider peaks and may be more likely to allow two similar species, with slightly different mobilities, to pass through to the sensor (a decrease in selectivity).

The length, l, of the analytical region 130 determines the duration of time in Equation 1. Longer analytical regions will cause losses in sensitivity due to increased chances for ions colliding with the filter electrodes 410. However, specificity may be increased because as the length increases, "equilibrium" must be met more precisely to pass all the way to the detection region 140.

The velocity of the carrier gas v determines the duration of time in Equation 1. If the gas flow is too fast and ions reach the detector plate before they have time to separate, there will be poor separation. If the gas flow is too slow, diffusion will continually cause the ions in equilibrium to diffuse to the parallel plates and be annihilated. Peak widths may also be wider in some instances when the flow of the carrier gas is too slow.

The frequency of the asymmetric waveform that determines the intensity of the electric field over time is contained within the function E(t). If the frequency is too low, then the distance traveled by the ions as they oscillate increases. As this distance becomes greater there is an increased chance of colliding with the parallel plates and decreasing sensitivity. This also can create narrower peaks in the spectra due to a decrease in the "effective gap," $d_e$. Higher frequencies have better sensitivity, but they may produce wider peaks in the DMS spectra.

The mobility at a field strength E is K(E). As discussed previously (see field strength E(t)), the mobility of an ion may be a function of the electric field, Mobility can also change as other environmental conditions change, such as moisture, pressure, and temperature. The mobilities under a single set of environmental conditions must be known for the current field strength (field strength parameter above).

The concentration of ions entering the analytical region 130 is n at t=0. The intensity value is a single number that is the sum of the positive and negative charged ions that hit the detector electrodes within the range of the "effective gap" de (oscillations will prevent ions from reaching the detector at the edges of the gap) over time.

The geometry of the analytical region 130 can be either flat plate or cylindrical. FIG. 4 depicts a flat plate design. A cylindrical design has cylindrical plates rather than flat parallel plates. Flat plate designs may have a uniform electric field throughout the analytical region, and the cylindrical plate design, has a nonuniform electric field. Equation 1 is able to simulate flat plate geometry because the uniform electric field is dependent only on time (t). However, for a cylindrical design the electric field will be a function of both time, for the asymmetric waveform, and location, for the non-uniform electric field. Cylindrical designs allow the use of a "resolution voltage" that allows peaks to be sharpened by adding an additional electric field (not used in Equation 1).

The diffusion coefficient (D in Equation 1) of an ion is a physical property of each ion that must be experimentally determined. Diffusion will also increase as temperature and pressure increase. Diffusion causes a loss of sensitivity and can cause wider peaks in the DMS spectra. Diffusion has a cumulative effect, so longer analytical regions (l) and slower drift velocities (v) will increase the effect of diffusion.

An increase in pressure increases ion mobility due to an increased number of collisions between ions. Increases in pressure also increase diffusion, which causes a loss of sensitivity if not for a larger increase in sensitivity due to a larger number of ions passing through the analytical region 130 (same concentration of ions at higher pressure=many more ions). The increase in diffusion (D in Equation 1) causes an increase in peak widths in the DMS spectra.

Complex ion chemistry occurs within the drift region as ions are repeatedly attracted together into clusters and broken apart as they move through the analytical region 130. If multiple compounds are present, new ion species may be created in the middle of the analytical region 130 that will quickly be annihilated because they will no longer be in equilibrium. Charge competition between different ion species may often prevent one of the species from creating more ions than the other.

An increase in temperature will cause a moderate increase in ion mobility. It also increases the rate of diffusion (less sensitivity and possibly wider peaks).

Ion mobility is also significantly influenced by moisture due to an induced dipole moment of an ion species that is caused by nearby water molecules. This increase in mobility is reflected in Equation 1 within K(E).

The shape of the asymmetric waveform is determined by the function E(t) in Equation 1. Different asymmetric waveforms can be made by changing the function E(t).

The parameters explained above are inputs in the analytical region 130 and are outputted as an intensity value, which is the integral of the ion concentrations that reach the detection region 140 over a specified amount of time. Several of these parameters are not simply numbers to be optimized, but are physical properties of ions or the collector electrodes 210. For example, the mobility of an ion at different field strengths is a physical property of ion species, and the diffusion rate is another physical property of each species (dependent on pressure and temperature).

The wave form generator 420, also shown in FIG. 4, may be controlled by a signal generator (not shown). Known signal generators may be used to achieve this purpose. The signal generator may generate an electric field between the filter electrodes 410 that is transverse to the carrier gas flow in the analytical gap—the space between the filter electrodes 410. As previously recited, the electric field between the filter electrodes 410 filters ion analytes based on various characteristics of the ions. The electric field may be an asymmetric radio frequency (RF) field, which also may be referred to as a filter field, a dispersion field, or a separation field. Field strength of the electric field may vary based on the applied asymmetric RF voltage (sometimes referred to as dispersion or separation voltage) and on the radial distance between the electrodes 410.

The signal generator uses various AC and DC voltages and frequencies to filter the ionized analytes within the carrier gas passing between the filter electrodes 410 in the analytical region 130. The signal generator may generate the electric field that biases ionized analytes of interest along a central path between the electrodes 410. As explained above, the alternative, asymmetric electric field transversely displaces ions between the electrodes 410, with each chemical species being displaced a distance toward the electrodes 410 per cycle of the electric field. Due to ions having different size and mass, the electric field may cause the ions not of interest to be attracted to either of the electrodes 410, which then neutralizes the ions not of interest from the carrier gas.

To form the electric field, the signal generator may generate an electrical waveform that passes through an amplifier (described below) and onto the filter electrodes 410. The signal generator may be battery operated or externally powered, for example. The electrical waveform may be an asymmetric radio frequency (RF) alternating current (AC) voltage, for example. The electrical waveform also may include a direct current (DC) voltage, which may be referred to as a compensation voltage. The compensation voltage reduces the alternating attraction to the filter electrode caused by the asymmetric RF AC voltage to maintain ionized analytes of interest on a central path between the filter electrodes 410. The amount of compensation voltage depends upon characteristics of the chemical species, and may be used to identify the presence or absence of a particular chemical species in the sample gas. The compensation voltage is applied to the electrodes 410 with the asymmetric RF voltage to compensate for the displacement of ions from a particular chemical species offsetting transverse displacement generated by the alternating asymmetric RF voltage. The compensation voltage reduces or substantially eliminates net transverse displacement of the ionized analytes of that chemical species, which enables those ionized analytes to pass between the filter electrodes 410. The ions that do not pass between the filter electrodes 410 undergo a net displacement and are neutralized on contact with either filter electrode 410.

Referring back to FIG. 2, after passing between the filter electrodes 410 and through the analytical region 130, carrier gas may transport the remaining filtered ionized analytes along a flow path to the detection region 150. The detection region 150 may comprise one or more collector electrodes 220 that are each electrically coupled to an amplifier 230. In an exemplary embodiment, there may be a positive detection mode and a negative detection mode in the detection region 140. The positive detection mode refers to positive ions passing through the filter electrodes 410 that are then detected by a negatively biased collector electrode 220. The negative detection mode refers to negative ions, passing through the filter electrodes 410, that are then attracted to and detected by a positively biased collector electrode 220. Having two collector electrodes 220, one positive and the other negative, enables simultaneous detection of positive and negative ion species, as positive and negative ions are generated in the ionization region 120 and are introduced into the analyzer region 130. It should be noted that certain chemical species may form both positive and negative ions in the ionization region 120. Data from both the positive and negative modes may be used in a single detection to identify the compounds in the sample.

When the positive and negative ions collide with one or the other collector electrodes 220, a charge may be deposited on the collector electrode 220. That charge may be amplified by respective amplifiers 230 to provide detection data for use in the signal processor 160 for identification of the detected ion species. The amplifiers 230 may measure the electrical current caused by the ionized analytes colliding with the collector electrodes 220 at a particular compensation voltage. The electrical current may be used to identify the presence or absence of a chemical species based on a comparison and matching with the electrical current response of known chemical species.

Figure 6A:
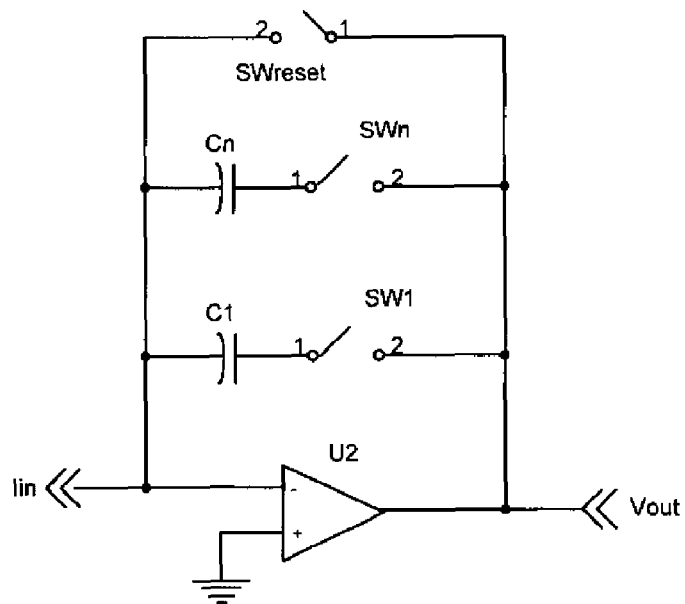
FIGS. 6A and 6B illustrate an exemplary embodiment of a capacitive trans impedance amplifier, and an exemplary timing diagram associated therewith, used in the device.

Each collector electrode may be connected to a dedicated amplifier. FIG. 6 shows an exemplary embodiment of the amplifier 230. In an exemplary embodiment, one or more amplifier 230 may be capacitive trans impedance amplifiers (CTIAs). Amplifiers of this type are particularly sensitive for reading out small charge quantities. Each CTIA amplifier 230 typically includes an operational amplifier having a negative input connected to an element and a positive input connected to an array offset bias voltage, which permits either positive or negative ions to be processed. The output of the amplifiers 230 may be fed back to the negative input through a feedback capacitor, having a value. Typical values for the capacitor of the CTIA amplifier 230 may be 3 picofarads (pF), 12 pF, 25 pF, or 50 pF. The output of the amplifiers 230 may be coupled to the input to the signal processor 150. The amplifier 230 takes a very small current input from the collector electrodes 220 and converts it into a voltage. In an exemplary embodiment, each amplifier 230 may have one or more feedback capacitors, $C_1$-$C_n$, and a normally open reset switch that is in parallel with the one or more feedback capacitors. The reset switch, when closed, may discharge the one or more capacitors. The output from each amplifier 230 may be sent to the signal processor 150. Typical values for the current deposited on the collector electrodes 220 may range from 10 pico amperes (pA) to 100 pA. Typical values for the voltage outputted by the amplifier 230 may be 0 volts (V) to 3 V. The voltage may be calculated using the transfer function shown in FIG. 6, $V_{out} = 1/C * \int_0^\tau 1_{in} * dt$. The voltage may be directed to the signal processor 150. There, the voltage may be converted in the signal processor 150 into a digital value using an analog-to-digital converter (ADC) module so that the digital magnitude can be processed by a digital processing module, such as a microprocessor or digital signal processor.

The amplifiers 230 may operate in two phases, and a controller (not shown) may control the timing of the amplifiers 230 in the two phases. The first phase may be defined when the amplifier 230 may be reset by closing the reset switch, thereby discharging the capacitors. The second phase may be defined when the voltage is integrated using the transfer function. The timing for the CTIA reset and integration phases may be synchronized by the microprocessor in the signal processor 150 to changes in the asymmetrical and compensation voltages applied to the analytical region 130. The CTIA is reset during transition changes until the voltage levels have settled. The integration phase starts after the voltage levels have settled. The CTIA amplifier prevents noise interference by synchronization of the CTIA reset and integration phases to changes in the analytical voltage levels so that voltage change transients are not integrated by the capacitors.

Figure 6B:
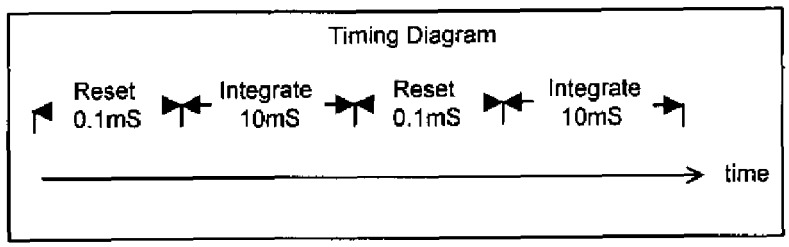

The integration time may be relatively short, e.g., on the order of milliseconds, as shown in FIG. 6B. In one exemplary embodiment, the integration time may be about 10 milliseconds or less. This integration time may be significantly shorter than the detection time in conventional TOF-IMS and DMS spectrometers. Moreover, with the CTIA amplifier, the gain may be changed depending on various environments.

For example, the CTIA amplifier gain may be increased by integrating over a longer period of time or by decreasing the value of integration capacitance. The gain may be lowered by integrating for a short time or increasing the net capacitance. An exemplary timing diagram is shown in FIG. 6B.

The amplifiers 230 amplify the current and send the output in voltage to the signal processor 150. The signal processor 150 may process the electrical current at the various compensation voltages in the compensation voltage range to identify a spectrum for the ionized analytes. The signal processor 150 may take the voltage from the one or more amplifiers 230 and convert it into a digital value. The signal processor may also operate in modes that correspond to the two phases of the amplifiers 230 to conserve energy. For example, when the amplifier 230 is in the integration phase, the signal processor may be in a "sleep" mode to conserve energy. In an exemplary embodiment, the signal processor 150 may only be in an "active" mode for the time it takes to receive data from the amplifiers 300, run a predictive algorithm, identify the compounds of interest, and send output to the readout display 160. At all other times, the signal processor 150 may be in "sleep" mode. Using a CTIA amplifier allows the signal processor to operate in multiple power saving modes.

The signal processor 150 may automatically vary the compensation voltage over a compensation voltage range for a given electric field to produce a spectrum of ionized analytes in the sample gas identifying the intensity of the ionized analytes at a particular compensation voltage. The spectrum of ionized analytes also may identify the intensity of any dopants or other molecules in the carrier gas. Intensity may refer to the amount of electrical current measured at a particular compensation voltage, for example. The compensation voltage range may be a range of voltages from a positive voltage to a negative voltage, between two positive voltages, or between two negative voltages. The spectrum of ionized analytes may be referred to as a mobility scan, an ionogram, or an ion spectra.

Chemical species within the carrier gas may be identified based upon correlation of the spectrum of the ionized analytes in the carrier gas with previously determined spectra for known chemical species. The spectrum of ionized analytes produces peaks based on an amount of electrical current detected at various compensations voltages. The spectrum of ionized analytes may be compared against stored spectra of known compounds and/or molecules for the device 100 based on the applied electric field to identify whether a match exists between the sample spectrum and any spectra of known chemical species. A match with a spectrum of a known chemical species may indicate that the sample gas includes the known chemical species.

In an exemplary embodiment, the signal processor 150 compares the spectrum for the ionized analytes with various spectra for known chemical species and may determine whether a match exists. If a match exists, the signal processor 150 may output data indicating that the sample gas contains one or more chemical species based on the match with the known spectrum or spectra. The output data indicating a match may be visible or audible on the readout display 160. If a match does not exist, the signal processor 150 may output data indicating that the sample gas does not match any known chemical species. Again, the output data indicating a non-match may be visible or audible on the readout display 160.

As recited above, temperature and moisture exert a substantial influence on ion behavior in DMS spectrometers. Specifically, moisture or humidity affect the peak locations of chemical species, and even though moisture can be controlled within some macroscopic range, very small changes in the humidity may cause the peaks to change location. To further assist with identifying species of interest, a prediction model may be used to predict the effect of moisture on peak locations of ions of interest. To accommodate these changes in peak location, the device 100 was adapted to accurately identify compounds and chemical species at various moisture levels. In an exemplary embodiment, an empirical model was developed using a known reactant ion peak (RIP) to accurately predict chemical species with the device 100 based on where that RIP appears. A predictive methodology may be used in the device that may be sensitive to changes in moisture or humidity levels, to identify peaks of interest in relationship to the RIP.

Figure 7A:
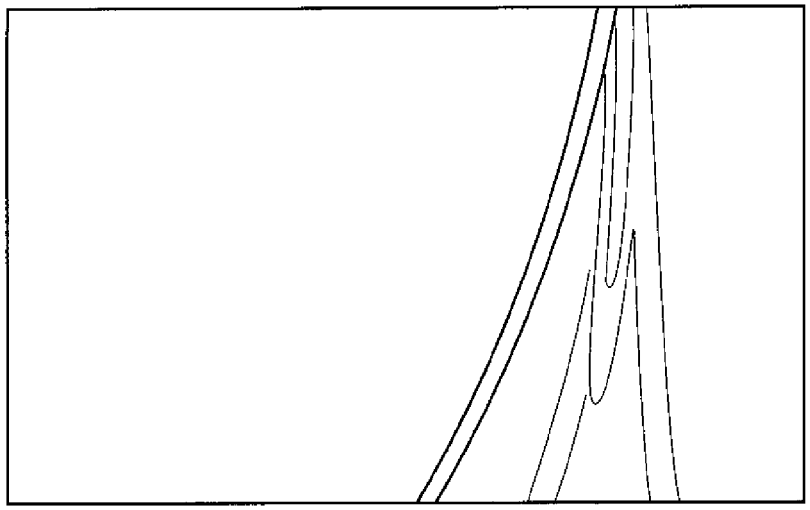
FIGS. 7A and 7B illustrate exemplary spectra of sample gas at dry conditions and wet conditions based on analyte analysis performed by an exemplary device.
Figure 7B:
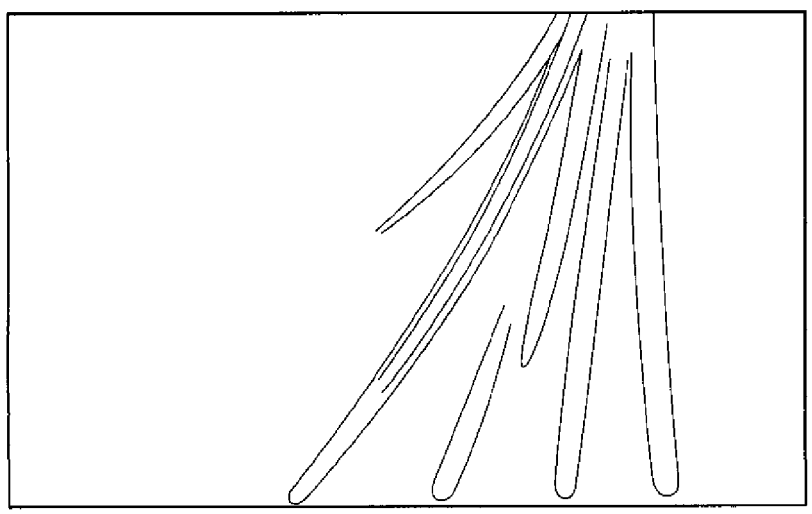

FIGS. 7A and 7B show the effect of moisture on the sample spectrum of the nerve agent GB. The nerve agent GB was measured at a variety of moisture levels to determine the effect of moisture on peak location. FIG. 7A shows a dry spectrum of GB, and FIG. 7B shows a wet spectrum of GB. As can be seen, the sample spectrum shows a shift in peak location simply based on the moisture level in the system. In DMS systems, this shift in peak location may lead to more accurate and reliable results because of the peak separation. However, the device 100 may be configured to predict the location of the peak of a chemical of interest depending on the level of moisture. To design the device 100 capable of accurately identifying chemical species regardless of the amount of moisture that results in different peak locations for a given species, an engineering model was developed to gather empirical data for chemical species at various moisture levels, a set of data was gathered, and a mathematical trend was determined for each agent of interest.

Figure 8A:
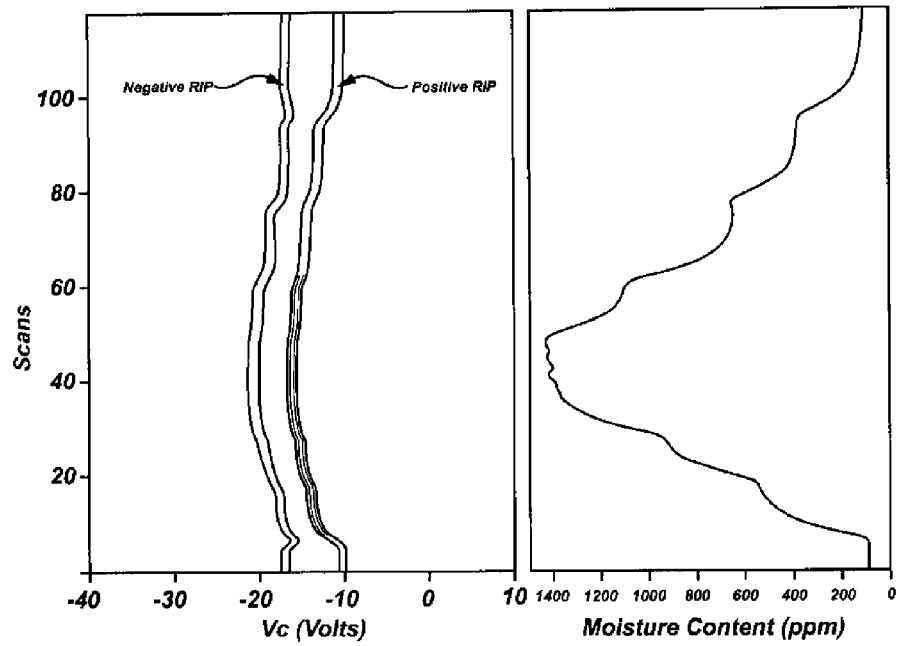
FIG. 8A illustrates reactant ion peak locations for a sample gas at various moisture levels.
Figure 8B:
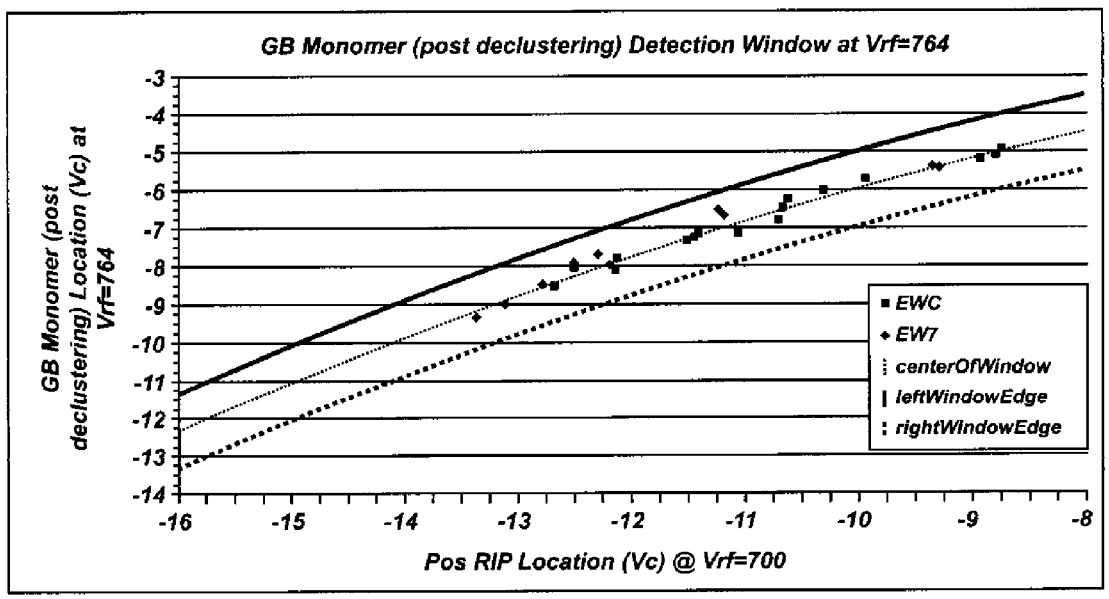
FIG. 8B illustrates a mathematical trend for reactant ion peak locations for a sample gas at various moisture levels.

FIG. 8A shows how the RIP moves as the moisture levels are changed from dry conditions, to wet conditions, back to dry conditions. The data collected for GB was then plotted in a graph, as shown in FIG. 5B, which displays the mathematical trend developed for a GB peak based on the moisture level. The centerline of the graph shows the relationship of the reactant ion peak to a GB peak. The outside bounds represent a statistical confidence level, which allows the device 100 to predict with confidence the existence of GB.

In an exemplary embodiment, this prediction methodology data, generated for all components whether chemical, biological, etc., may be stored in the device 100. This data allows the device 100 to accurately predict the existence of chemical species under the influence of moisture (which relates to the humidity in the air). The prediction methodology enables the device 100 to predict the peak location of chemical species when the RIP location is known. In other words, in an unknown environment, the known RIP may be determined, and from that, using the mathematical trend programmed in the device 100, analytes may be detected based on the stored data.

Figure 9:
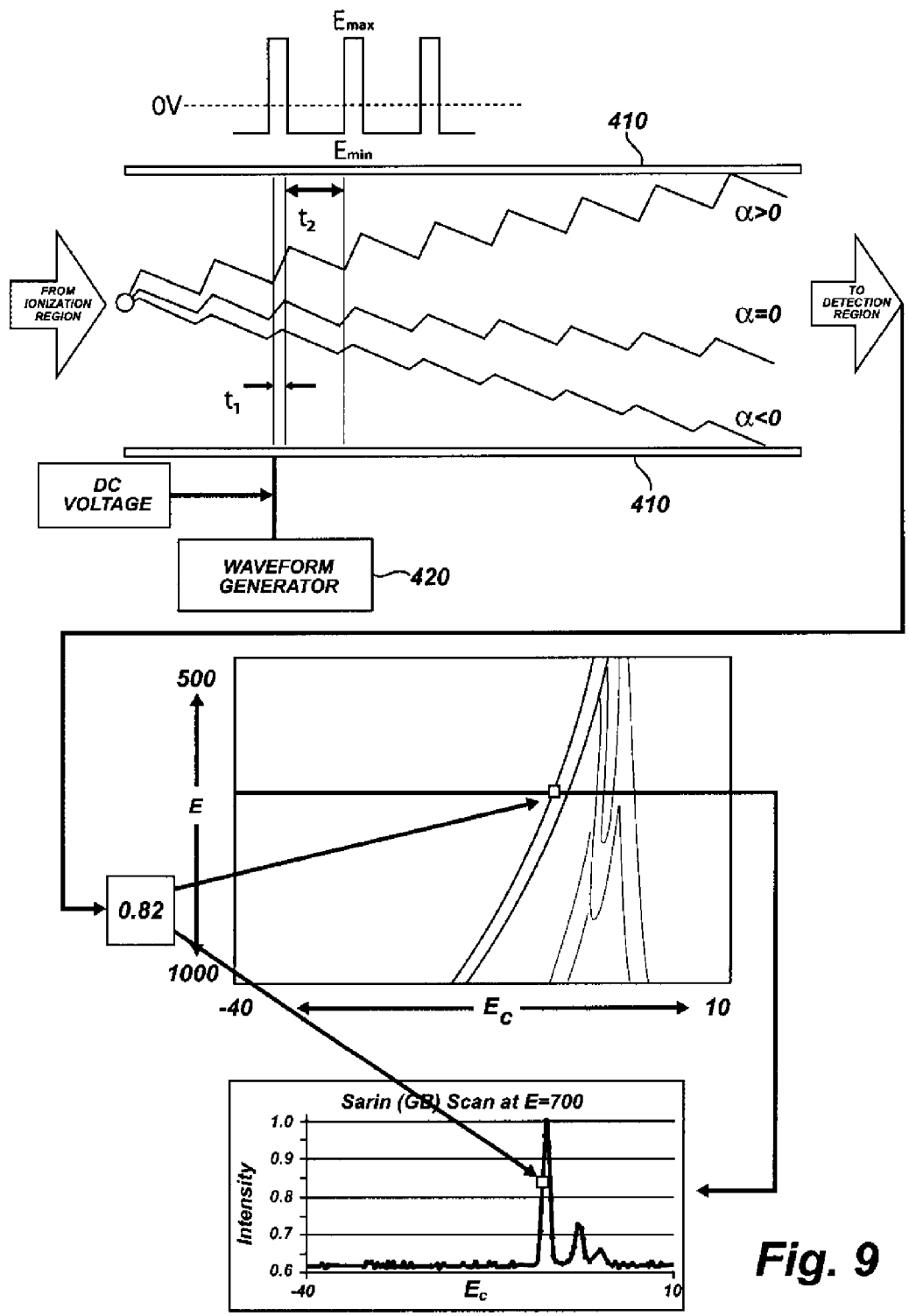
FIG. 9 illustrates exemplary spectra of sample gas generated based on analyte analysis performed by an exemplary device.

FIG. 9 illustrates an exemplary embodiment of a spectrum of ionized analytes in a carrier gas. FIG. 9 illustrates a spectrum generated based on GB ions included in the carrier gas with the ion intensity being identified on the vertical axis (i.e., y axis), and the compensation voltage being identified on the horizontal axis (i.e., x axis) of the bottom plot for a specific dispersion voltage. FIG. 9 illustrates detected GB ions forming a peak intensity at a compensation voltage around −18 volts. Future detections of a peak at this compensation voltage may indicate detection of GB in the sample gas.

Figure 10:
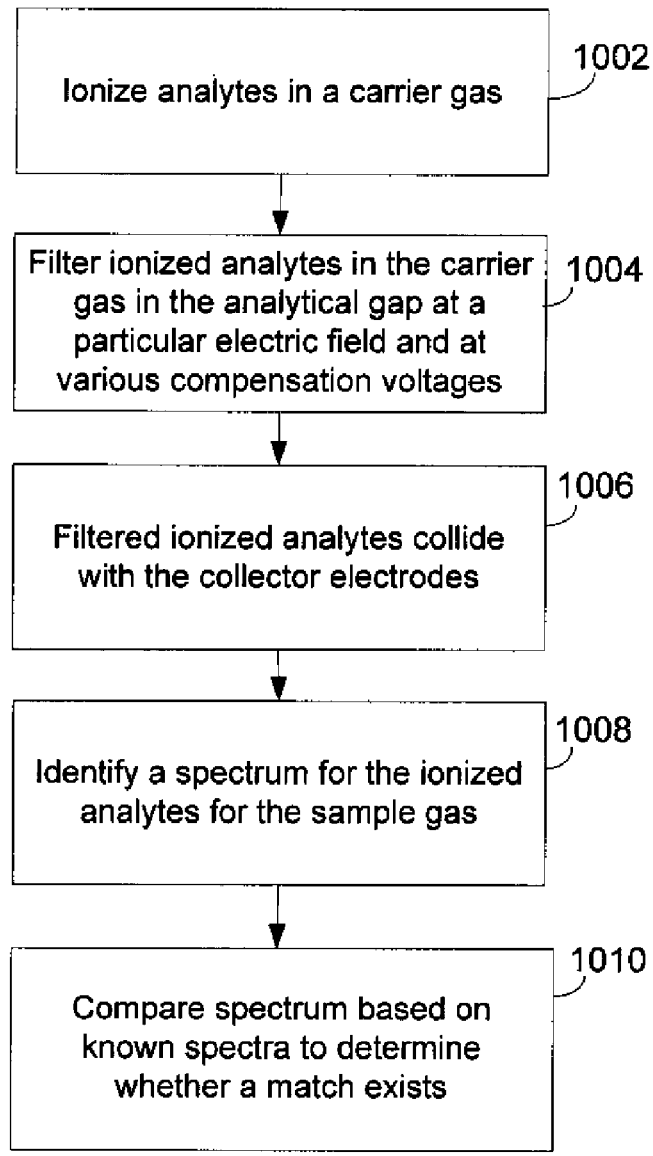
FIG. 10 illustrates an exemplary block diagram for detecting chemical species based on analytes in a carrier gas using an exemplary device.

FIG. 10 illustrates a flow diagram of an exemplary method 1000 for detecting chemical species based on analytes in a carrier gas, according to an exemplary embodiment of the device 100. This exemplary method 1000 is provided by way of example, as there are a variety of ways to carry out methods according to the present disclosure. The method 1000 shown in FIG. 10 can be executed or otherwise performed by one or a combination of various systems. The method 1000 is described below as carried out by the device 100, as described above, and various elements of the device 100 are referenced in explaining the example method of FIG. 10. Each block shown in FIG. 10 represents one or more processes, methods, and/or subroutines carried out in the exemplary method.

In 1002, the device 100 receives sample gas. For example, a sample gas enters the inlet system 110 from an ambient environment. The inlet system may comprise a membrane 206 to selectively separate analytes of interests and filter the sample gas.

In 1004, sample gas is ionized. For example, the sample gas may be ionized over an ionization source, such as Ni63, to generate ions.

In 1006, ions are filtered in the analytical region 130. For example, the ions may be carried by a carrier gas through two filter electrodes that apply an asymmetric, alternating electric field and a compensation field to separate the ions. The signal generator may be used to generate the electric field along with various compensation voltages over a compensation voltage range between the filter electrodes in the analytical region for filtering ionized analytes within the carrier gas.

In 1008, the ions are detected. For example, the filtered ions may be transported in the carrier gas and collide with the collector electrodes. The collision generates an electrical current by transferring the charge of the ionized analytes to the collector electrodes. Each collector electrode may be connected to a CTIA amplifier for converting the charge into voltage.

In 1010, the signal processor digitizes the information from the CTIA amplifier and compares the spectrum for the ionized analytes with various spectra for known chemical species and may determine whether a match exists. For example, the signal processor may be programmed with a predictive methodology algorithm capable of identifying species at various moisture levels.

Figure 11:
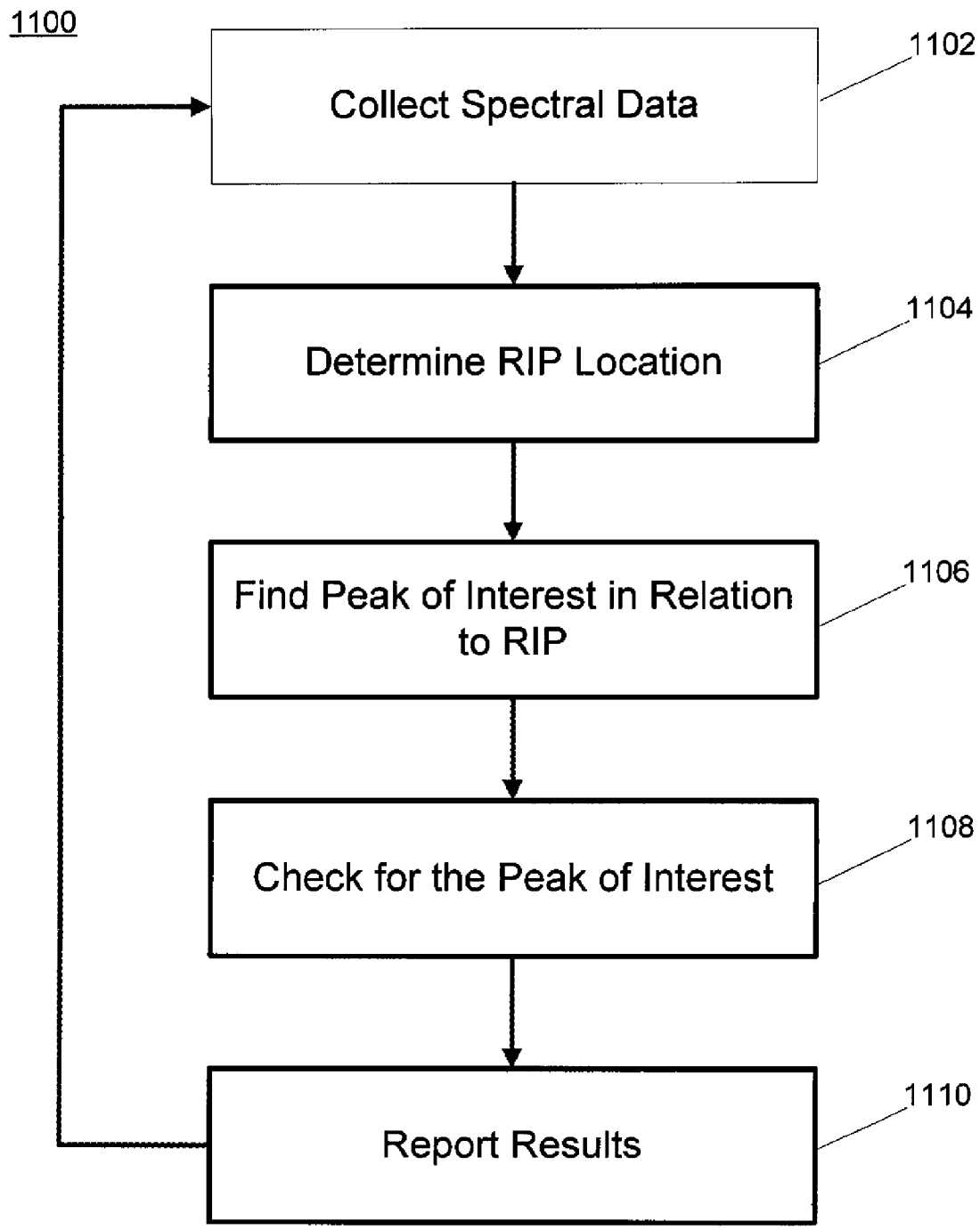
FIG. 11 illustrates an exemplary block diagram of an algorithm process to identify an ion species based using a known reactant ion peak.

FIG. 11 illustrates a flow diagram of an algorithm process 1100 to identify an ion species based using a known reactant ion peak, according to an exemplary embodiment of the device 100. This exemplary process 1100 is provided by way of example, as there are a variety of ways to carry out processes according to the present disclosure. The process 1100 shown in FIG. 11 can be executed or otherwise performed by one or a combination of various systems. The method 1100 is described below as carried out by the device 100, as described above, and various elements of the device 100 are referenced in explaining the example method of FIG. 11. Each block shown in FIG. 1I represents one or more processes, methods, and/or subroutines carried out in the exemplary method.

The process 1100 begins at step 1102 when spectral data is collected for chemical species at various moisture levels. In step 1104, a RIP location is determined for chemical species at each moisture level. In step 1106, the reactant ion peak of a chemical species of interest is found in the device 100 by using methods described above. In step 1108, the chemical species of interest is detected based on stored data. In step 1110, the results (chemical identification) is sent to a readout display where they may be audibly or visibly displayed.

It will be apparent to those skilled in the art that various modifications and variations can be made in the method of manufacture of the present invention and in construction and use of this vapor detector without departing from the scope or spirit of the invention. Other embodiments of the invention will be apparent to those skilled in the art from consideration of the specification and practice of the invention disclosed herein. It is intended that the specification be considered as exemplary only, with a true scope and spirit of the invention being indicated by the following claims.

Accordingly, while the present invention has been described here in detail in relation to its exemplary embodiments, it is to be understood that this disclosure is only illustrative and exemplary of the present invention and is made to provide an enabling disclosure of the invention. Accordingly, the foregoing disclosure is not intended to be construed or to limit the present invention or otherwise to exclude any other such embodiments, adaptations, variations, modifications and equivalent arrangements.

What is claimed is:

1. A method for identifying chemical species in a sample, the method including the steps of:
   introducing a sample gas into a differential ion mobility device;
   ionizing at least a portion of the sample gas to generate at least one ion species;
   filtering the at least one ion species between a pair of filter electrodes;
   generating a detection signal using a capacitance trans impedance amplifier (CTIA) in response to the at least one ion species depositing a charge on a collector electrode, the CTIA sending the detection signal to a signal processor;
   detecting a spectral peak associated with the at least one ion species by processing the detection signal; and
   utilizing a prediction model to predict a moisture effect on the at least one ion species and referencing a data store to identify an unknown compound in the species.

2. The method of claim 1, wherein the sample gas is introduced from an ambient environment.

3. The method of claim 1, wherein filtering the at least one ion is performed by applying an asymmetric, alternating electric field adapted to influence the mobility behavior of the at least one ion species traveling between the pair of filter electrodes.

4. The method of claim 3, wherein the substantially asymmetric, alternating electric field is controlled by a signal generator that selectively adjusts the field and causing the at least one ion species to be separated.

5. The method of claim 1, wherein the CTIA comprises an input for receiving a current signal from the collector electrode and an output for outputting a voltage signal to a signal processor, and at least one feedback charge storage capacitor coupled between the input and output.

6. The method of claim 5, wherein the CTIA comprises at least one reset switch coupled between the input and output and in parallel with the at least one feedback charge storage capacitor, the at least one feedback charge being discharged in response to the reset switch periodically being activated, thereby ending an integration period.

7. The method of claim 1, wherein the CTIA operates in an integration phase and a reset phase, the integration phase adapted to integrate the CTIA over a period of time, and the reset phase adapted to discharge the at least one capacitors, the CTIA being operatively coupled to a controller for controlling the timing of the integration phase and reset phase.

8. The method of claim 6, wherein the CTIA comprises at least one additional capacitor in parallel with at least one feedback charge storage capacitor to vary the gain of the CTIA.

9. The method of claim 1 further comprising the step of conveying the detected spectral peak either audibly or visibly to a display.

10. A device for identifying chemical species in a sample gas, the device comprising:
    an inlet adapted to receive a sample gas, the inlet being selectively separated from an ionization region that ionizes the sample gas to generate ions;
    a filter having at least a pair of oppositely disposed filter electrodes defining an analytical gap between which a substantially asymmetric field is generated, the substantially asymmetric field being controllable by a signal generator, wherein the filter separates the ions based on ion mobility characteristics;
    at least one collector electrode adapted to receive the ions, the collector being coupled to an capacitive trans impedance amplifier (CTIA);
    a prediction model adapted to predict a moisture effect on the ions;
    a signal processor adapted to receive an output voltage generated by the CTIA in order to detect a spectral peak associated with the ions; and
    a data store for identifying an unknown compound in the species.

11. The device of claim 10, wherein the filter applies a compensation field as a DC voltage in addition to the asymmetric field, the filter comprising a range of the applied substantially asymmetric field and compensation field.

12. The device of claim 11, wherein the substantially asymmetric field and the compensation field are controlled by a signal generator to change with substantially asymmetric field and the compensation field with time.

13. The device of claim 10, wherein the CTIA comprises an input for receiving a current signal from the collector electrode and an output for outputting a voltage signal to a signal processor, and at least one feedback charge storage capacitor coupled between the input and output, the first feedback charge storage capacitor having a value.

14. The device of claim 10, wherein the CTIA comprises at least one reset switch coupled between the input and output and in parallel with the first feedback charge storage capacitor, the reset switch periodically discharging the at least one feedback charge storage capacitor to start a new integration period.

15. The device of claim 14, wherein a controller is adapted to synchronize the CTIA to reset at the time in which the asymmetric field and compensation fields are changed within the filter.

16. The device of claim 15, wherein the CTIA remains in a reset state until the asymmetric field and compensation fields are changed within the filter so as to substantially reduce noise sent to the CTIA during the filter changes.

17. The device of claim 14, wherein the controller is adapter to synchronize the CTIA to begin the integration phase after the asymmetric field and compensation fields are in a steady state condition.

18. The device of claim 10 comprising a readout display configured to display, either visibly or audibly, the detected spectral peak.

19. The device of claim 14, wherein the device sensitivity and selectivity can be dynamically adjusted in real-time by increasing or decreasing the integration phase of the CTIA or increasing or decreasing the integration capacitor(s) of the CTIA.

20. The device of claim 14, wherein an array of CTIAs is used.

21. The device of claim 10, wherein the inlet is heated.

* * * * *